(12) United States Patent
Trygstad

(10) Patent No.: US 8,751,167 B2
(45) Date of Patent: Jun. 10, 2014

(54) SYSTEM AND METHOD FOR ALKYLATION PROCESS ANALYSIS

(75) Inventor: W. Marcus Trygstad, Spring, TX (US)

(73) Assignee: Invensys Systems, Inc., Foxboro, MA (US)

( * ) Notice: Subject to any disclaimer, the term of this patent is extended or adjusted under 35 U.S.C. 154(b) by 1355 days.

(21) Appl. No.: 12/509,212

(22) Filed: Jul. 24, 2009

(65) Prior Publication Data

US 2010/0023275 A1   Jan. 28, 2010

Related U.S. Application Data

(60) Provisional application No. 61/084,142, filed on Jul. 28, 2008.

(51) Int. Cl.
*G06F 19/00* (2011.01)
(52) U.S. Cl.
USPC ............ 702/25; 702/22; 702/24; 73/61.44; 73/61.43; 436/105; 436/142; 436/143
(58) Field of Classification Search
USPC ............ 702/25, 22, 24; 436/105, 142, 143; 73/61.44, 61.43
See application file for complete search history.

(56) References Cited

U.S. PATENT DOCUMENTS

| | | |
|---|---|---|
| 3,653,835 A | 4/1972 | Brandel |
| 4,009,998 A | 3/1977 | Benningfield, Jr. |
| 5,583,049 A | 12/1996 | Altman et al. |
| 5,583,275 A | 12/1996 | Kranz et al. |
| 5,751,415 A | 5/1998 | Smith et al. |
| 6,096,553 A | 8/2000 | Heald et al. |

OTHER PUBLICATIONS

Non-Final Office Action dated Sep. 10, 2012 regarding U.S. Appl. No. 13/420,175, 14 pages.
SpectrOn NIR Refinery Monitor, Datasheet (online), Guided Wave, Inc., 2006 (retrieved on Oct. 1, 2009) Retrieved from the Interent <URL:http://web.archive.org/web20061129021719/http://www.guided-wave.com/products/spectrometers/spectron_refinery_monitor/> Entire document, especially para 3 (Applications) and para 9 (Analyzer).
Friedman, Y. "Engineering Models For Inferential Controls". Process Optimization Conference, Marriott Houston Westside, Houston Texas, Apr. 7-10, 1997, By Gulf Publishing Company and Hydrocarbon Processing [online],retrieved on Oct. 1, 2009] Retrieved from the interenet <URL: http://www.petrocontrol.com/pdf/1997_ENG_models.pdf> Entire document, especially p. 8, para 1.

*Primary Examiner* — Jonathan C. Teixeira Moffat
*Assistant Examiner* — Hien Vo
(74) *Attorney, Agent, or Firm* — Edward S. Jarmolowicz, Esq.

(57) ABSTRACT

A method and apparatus is provided for concentration determination of at least one component in an acid catalyst for hydrocarbon conversion containing an unknown concentration of an acid, an acid-soluble-oil (ASO), and water. An instrument configured for measuring a property of the acid catalyst, has responsivities to concentrations of one of the acid, ASO, and water, substantially independent of the concentrations of the others of the acid catalyst, ASO, and water. A temperature detector is configured to generate temperature data for the acid catalyst. A processor is configured to capture data generated by the temperature detector and the instrument, and to use the data in combination with a model to determine a temperature compensated concentration of the one of the acid, the ASO, and the water. Optionally, one or more other instruments configured for measuring other properties of the liquid mixture may also be used.

21 Claims, 7 Drawing Sheets

SYSTEM AND METHOD FOR ALKYLATION PROCESS ANALYSIS

RELATED APPLICATION

This application claims the benefit of U.S. Provisional Application Ser. No. 61/084,142 entitled Multi-Property Measurement, filed on Jul. 28, 2008, the contents of which are incorporated herein by reference in their entirety for all purposes.

BACKGROUND

1. Technical Field

This invention relates to chemical analysis, and more particularly to alkylation process analysis and control.

2. Background Information

Introduction to the Refining Alkylation Market

Between a quarter and a third of the world's refineries operate alkylation units, which convert relatively low-value byproducts of the crude oil refining process into alkylate, a high octane component used to make gasoline. Among the numerous control variables that determine the economics of alkylation is the composition of the acid catalyst. Globally, the number of alkylation units using hydrofluoric acid (HF) is currently about 125 versus about 90 using sulfuric acid ($H_2SO_4$ or SA). Slightly more than half of all alkylation units in the world are located in North America, where gasoline is favored over diesel as a motor fuel for passenger cars and alkylate is accordingly a valued blending component.

Another important application of alkylation technology is in the production of LABs (linear alkyl benzenes), important as a raw material used in laundry detergents. However, the total number of alkylation units in operation to produce LABs, as well as tonnage produced, is rather small compared with the refining industry.

Background: Alkylation Process Control

Alkylate is one of the most important gasoline blending components in the refining industry. Because it has an extremely high octane number, contains virtually no sulfur, and can be produced using olefinic by-products from the fluidized catalytic cracking (FCC) unit, alkylate has been called refiners' gold. Given that the reactants are seldom pure, and that propylene is sometimes mixed with the olefin feed, alkylate in practice comprises a mixture of compounds instead of pure isooctane as depicted in the following idealized equation:

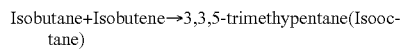

Isobutane+Isobutene→3,3,5-trimethypentane(Isooctane)

Produced in a continuous-flow process, the chemical addition of isobutane and isobutene is effected conventionally through liquid phase catalysis involving strong acids such as hydrofluoric acid (HF) and sulfuric Acid ($H_2SO_4$, or SA), although solid phase catalysts are currently under development.

Monitoring and controlling the composition of the liquid acid catalyst, i.e., acid strength and the levels of impurities that dilute the acid, are among the most important challenges associated with the profitable operation of the alkylation process. One important impurity is water, which enters the process with the feed streams. Though present at ppm (parts per million) levels, water accumulates in acid catalyst at percent levels due to feed rates ranging from a few thousand barrels per day (bpd) to tens of thousands of bpd. By contrast, acid soluble oil (ASO, as defined hereinbelow) accumulates in the acid catalyst, a by-product of reactions involving feed impurities that contain sulfur, oxygen, or conjugated double bonds.

HF Alkylation

In the case of HF alkylation (HFA), water generally is controlled at levels below 2% to minimize corrosion of equipment in the unit. Also, total hydrocarbons dissolved in the catalyst are typically held at levels around 11%-16% to yield alkylate of the required quality and maximize process economics. In HFA, HF strength is controlled through acid regeneration within the alkylation unit, which is essentially a distillation process that separates HF from the higher-boiling impurities, $H_2O$ and ASO (Acid Soluble Oil, as defined hereinbelow).

If HF strength drops below about 80%, side reactions can accelerate and lead to a condition called acid runaway, which consumes HF and produces large amounts of ASO. Such runaways rarely occur, as unit operators usually have time to detect the incipient runaway and "pull charge" (withhold olefin feed) to stop the process before the runaway condition actually occurs. However, this action also stops the production of alkylate while the catalyst is regenerated. Furthermore, acid regeneration itself has associated costs including energy required to run the unit, neutralization and disposal of hydrocarbon byproducts, and the addition of fresh, pure HF. Thus, the ability to monitor and control catalyst composition in real time allows refiners to avert runaways, reducing operating costs while also tending to maximize product quality (octane), throughput, and the time between maintenance shutdowns to repair or replace corroded components.

SA Alkylation

SA alkylation (SAA) differs from HFA in that the catalyst generally is not, with rare exception, regenerated on site at the refinery. HF has a relatively low boiling point and can be distilled. By contrast, SA is essentially non-volatile and therefore cannot be purified through distillation. Rather the "spent" acid generally must be shipped by rail car for remote processing. Thus, the high cost associated with off-site regeneration partially offsets the perceived safety advantage of SA over HF, i.e., its low volatility.

Given that the alkylation reaction occurs only when acid strength is sufficiently high to catalyze the reaction of isobutane with olefins, the effectiveness of SA diminishes when its strength falls below a certain level due to accumulation of ASO and $H_2O$—typically around 88%-90%. Thus, the economics of SA alkylation depend on knowing exactly the point where SA becomes too weak and must be taken out of service. For example, taking SA out of service when its strength is 89% may be very costly if good quality alkylate can be produced economically with acid strength≥88.5%.

Traditional Analysis of Acid Catalyst

The composition of acid catalyst is typically determined by manually obtaining a sample for analysis in the local refinery laboratory daily, weekly, or several times each week. In contrast with hydrocarbon samples routinely analyzed in the refinery lab, full analysis of acid catalyst samples tends not to be straightforward due to special requirements for sample handling, preparation, and analysis. Additionally, HF presents a safety hazard due to its volatility and toxicity. With both HF and SA, comprehensive determination of composition is difficult for at least two reasons. First, measurement of water generally depends on a Karl Fischer titration method specially modified to neutralize the strong acid. Second, ASO is not a single compound, but includes a range of chemically-related compounds that have a rather wide range of molecular weights and boiling points, some of which (e.g., "light ASO") can evaporate rapidly at room temperature.

Analysis Frequency

In consideration of the foregoing difficulties, refiners may test the acid as infrequently as possible to minimize laboratory workload. Some refiners make do with one analysis per week while refineries operating in Los Angeles County, Calif. may be required by regulation to test HF catalyst once every 8 hours. Infrequent analysis may be sufficient to permit process control under stable operating conditions, but not to identify rapid changes caused by occasional surges in feed impurities that lead to generation of ASO.

Analytical Reproducibility and Completeness

Compounding the issue of analysis frequency, laboratory test results may not always be reliable due to the difficulty of obtaining a representative sample when sample volumes are minimized in consideration of safety, as may be done in the case of HF catalyst. This further compounds the difficulty of reproducibly executing the test method itself. And if technicians running the tests do not routinely perform the Karl Fischer water measurement, acid strength measured by titration may be the only parameter known in regard to catalyst composition, severely limiting operators' ability to optimize the process.

Safety

As mentioned, HF is both volatile and toxic. Sampling, sample handling, and testing therefore are executed in accordance with audited procedures carefully designed to ensure the safety of operators and technicians. In the case of HF, testing frequency may be deliberately suppressed to minimize exposure risks.

All of this underscores the undesirability of manual methods for routine analysis. Attempts have been made to replace manual sampling and testing with online measurement techniques, to facilitate the efficient and safe operation of alkylation units. To date, however, these attempts have generally been unsatisfactory, e.g., due to incomplete or inaccurate measurements by simple univariate instruments; or due to excessive complexity, lower-than-desired reliability and/or relatively high costs, such as associated with conventional use of spectrometric technologies. Thus, a need exists for an improved analyzer system for real-time alkylation process analysis and control.

SUMMARY

According to one aspect of the invention, an apparatus is provided for on-line concentration determination of at least one component in a liquid mixture flowing through an alkylation process, which liquid mixture is an acid catalyst for hydrocarbon conversion containing an unknown concentration of an acid, an acid-soluble-oil (ASO), and water. The apparatus includes an instrument configured for measuring a property of the liquid mixture, the instrument having responsivities to concentrations of one of the acid, ASO, and water, substantially independent of the concentrations of the others of the acid catalyst, ASO, and water. A temperature detector is configured to generate temperature data for the liquid mixture; and a processor is configured to capture data generated by the temperature detector and the instrument, and to use the data in combination with a model of responsivities to various concentrations of the acid, ASO, and water at various temperatures, to determine a temperature compensated concentration of the one of the acid, the ASO, and the water, in the liquid mixture.

In another aspect of the invention, an apparatus is provided for on-line determination of levels of at least three properties in a liquid mixture which contains unknown levels of the properties. The apparatus includes a first instrument configured for measuring a first property of the liquid mixture, and a second instrument configured for measuring a second property of the liquid mixture. The first and second instruments are configured to have mutually distinct responsivities to levels of the properties. A processor is configured for capturing data generated by the first and second instruments and using the data in combination with a model of responsivities to various levels of the properties at various temperatures, to determine levels of the properties in the liquid mixture.

In yet another aspect of the invention, a method is provided for on-line concentration determination of at least one component in an acid catalyst for hydrocarbon conversion containing unknown concentrations of an acid, an acid-soluble-oil (ASO), and water. The method includes supplying the acid catalyst to an instrument configured to have responsivities to concentrations of one of the acid, ASO, and water, substantially independent of the concentrations of the others of the acid catalyst, ASO, and water. The acid catalyst is supplied to a temperature detector, and a property of the liquid mixture is measured using the instrument. A processor captures data generated by the instrument and temperature detector, and uses the data in combination with a model of responsivities to various concentrations of the acid, ASO, and water at various temperatures, to generate a temperature compensated concentration of at least one of the acid, the ASO, and the water, in the acid catalyst.

In still another aspect of the invention, a method is provided for on-line concentration determination of the composition of a liquid mixture which contains unknown levels of at least three components. The method includes supplying the liquid mixture to at least first and second instruments having mutually distinct responsivities to levels of the three components, measuring a first property of the liquid mixture using the first instrument, and measuring a second property of the liquid mixture using the second instrument. Data generated by the first and second instruments is captured and used in combination with a model of responsivities to various levels of the components at various temperatures, to determine levels of the at least three components in the liquid mixture.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
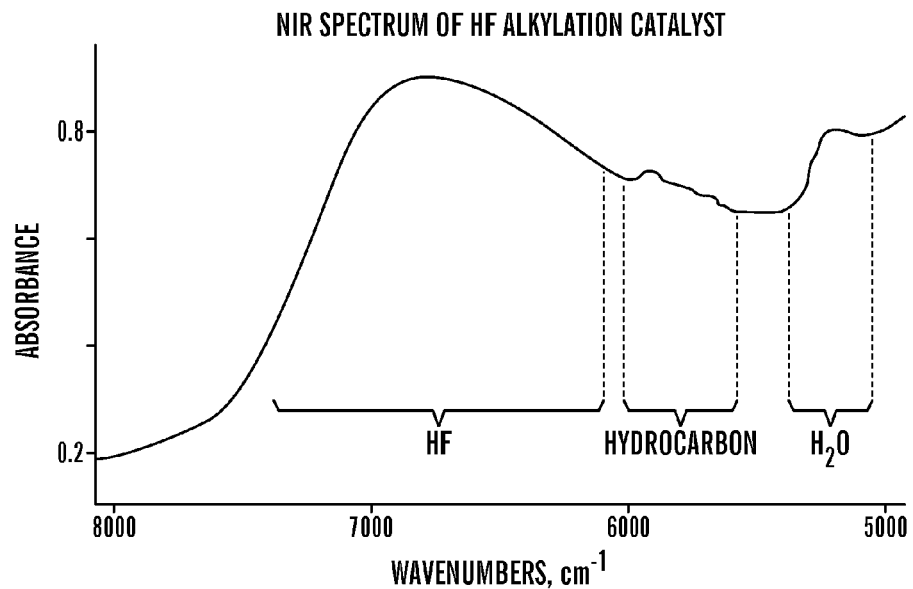
FIG. 1 is a plot of an NIR spectrum of HF Alkylation Catalyst.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. In addition, well-known structures, circuits and techniques have not been shown in detail in order not to obscure the understanding of this description. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

General Overview

This disclosure describes a system and method for (e.g., online) composition measurement of acid catalyst used in alkylation units of the type currently operating in roughly 30% of the world's oil refineries. Compared with available spectrometric technologies, embodiments of the present invention substantially satisfy requirements for broad adoption by refiners globally: ease of implementation, analytical reliability (accuracy), operational reliability (low maintenance), and cost-effectiveness. Particular embodiments do so by combining two or more relatively low-cost sensor devices that tend to be both simple and inexpensive compared with conventional spectrometers. As will be discussed in greater detail hereinbelow, examples of such relatively low-cost sensor devices include, but are not limited to, the Foxboro 871FT toroidal conductivity sensor and the CFS10 Coriolis flowmeter, both available from Invensys Systems, Inc. (Foxborough, Mass., USA). Other embodiments enable the use of spectrometers without the need for relatively complex and expensive isothermal sample conditioning.

Where used in this disclosure, the term "property" refers to chemical and/or physical characteristics of a material, independently of its relative concentration within a mixture. The terms "computer" and "processor" are meant to encompass a workstation, personal computer, personal digital assistant (PDA), wireless telephone, or any other suitable computing device including a microprocessor, a computer readable medium upon which computer readable program code (including instructions and/or data) may be disposed, and a user interface. The terms "data system" and "model" are intended to refer to a computer-related component, including hardware, software, and/or software in execution. For example, a model may be, but is not limited to being, a process running on a processor, a processor including an object, an executable, a thread of execution, a mathematical equation or set of equations, a program, and a computer. Moreover, the various components may be localized on one computer and/or distributed between two or more computers. The terms "real-time" and "on-demand" refer to sensing and responding to external events nearly simultaneously (e.g., within milliseconds or microseconds) with their occurrence, or without intentional delay, given the processing limitations of the system and the time required to accurately respond to the inputs. As used herein, the term "acid catalyst" refers to a liquid mixture (e.g., single phase) including an acid (HF or SA), water, and dissolved hydrocarbon (ASO). It is noted that the "acid strength" of the acid catalyst is commonly defined as the concentration of the acid, and while the acid can function as a catalyst on its own, as a practical matter, and as used herein, acid catalyst is understood to comprise the ternary mixture. As used herein, the term "ASO" or "acid-soluble oil" refers to substantially any hydrocarbon that has been dissolved within an acid, alone or in combination with additional hydrocarbon that may have been emulsified or otherwise mixed with acid in a liquid sample or on-line process. For example, the term ASO (or "polymer") refers primarily to hydrocarbon that has been dissolved, emulsified or otherwise mixed with HF or SA to form to form a nominally single-phase mixture that persists as such during online sampling and analysis. By contrast, the acid catalyst sample may contain entrained light hydrocarbon, believed to be substantially isobutane, in the form of phase-separated liquid or gas (IB/ps), either of which can be readily removed from the bulk acid catalyst by means of a device of suitable design (e.g., a separator).

Referring now to FIGS. 1-9, embodiments of the present invention will be more thoroughly described.

Criteria for an Online Analysis Solution

To overcome the issues of manual sampling and testing, the instant inventor has sought an online analytical methodology which is relatively straightforward to implement, reliable (mechanically robust with respect to acid), sufficiently accurate to support process optimization objectives, simple in overall design and operation, and cost-effective.

Additionally, installation of an online analyzer should not simply exchange one set of risks for another. For example, maintenance technicians who previously had no exposure to HF may be required to service an HF analyzer. Thus, solving the analytical problem should also enhance safety and reduce the overall risk of operator exposure.

A Question of Information Channels

Technologies that may be used with the embodiments disclosed herein generally fall into either of two classes: single-channel measurement instruments; and multi-channel spectrometers. The following Table 1 provides a representative comparison.

TABLE 1

Comparison of Technologies Applied for analysis of Alkylation Catalyst.

| | INSTRUMENTS | SPECTROMETERS |
|---|---|---|
| DESCRIPTION | Devices employing technology that responds directly and proportionately to variation in a specific physical or chemical property in the sample, or measures | Devices that measure a spectrum, which in the general sense is a plot of response (intensity) across a number of channels normally defined in terms of frequency (or |

TABLE 1-continued

Comparison of Technologies Applied for analysis of Alkylation Catalyst.

| | INSTRUMENTS | SPECTROMETERS |
|---|---|---|
| | the response of such a property to a stimulus that it applies to a sample. | wavelength). The response is a measure of the interaction of electromagnetic energy applied to the sample by the spectrometer at specific frequencies, or of the emission of energy by the sample in response to the application of electromagnetic energy. |
| CHARACTERISTICS | On the whole, instruments are simple, compact, have relatively low cost, and generally require no sample conditioning, but analyze a stream as presented. Instruments generally are univariate devices that supply a single channel of information in response to a specific chemical or physical change, but are not suitable for measuring an effect that has two or more causes. | Complex compared with instruments, costing 20-50 times as much as instruments and usually requiring sample conditioning, e.g. to remove phase-separated water or particulates or to provide tight temperature control. Examples: NIR (near infra-red) and NMR (nuclear magnetic resonance) spectroscopy. By definition, spectrometers are multi-channel, multi-variable analyzers. |
| CALIBRATION, MATHEMATICS | Generally, the calibration is a simple mathematical function applied to the instrument's output in response to a physical or chemical property of interest. Sometimes it is as simple as standardizing on two materials to define zero and span. The instrument stability is generally stable enough to permit this calibration equation to be used for a long period of time. | Calibration normally relies on multi-variable chemometrics to build property models that are applied to the spectra of unknown samples for property prediction. As a secondary or "referenced" methodology, modeling requires a significant population of samples on which lab tests have been performed, and for which spectra have been measured. |
| EXAMPLES | pH probes and ion-selective electrodes; viscometers; refractive index probes; beta gauges; densitometers; conductivity meters; simple photometers; flow meters; various water cut measurement technologies; temperature probes (RTDs) | NIR, FTNIR (Fourier Transform NIR), Raman, and NMR spectrometry |
| APPLIED TO THE ANALYSIS OF ACID CATALYST | Refractive Index Densitometry Conductivity | FTNIR (for HF) Process NMR (for $H_2SO_4$) |
| LIMITATION | Univariate data (too little information: one equation but three unknowns) | High cost; sampling system complexity (to control temperature); installation complexity (fiber optics for NIR) |

Individual instruments referenced above are relatively simple, low cost, easy to implement, and functionally reliable but have heretofore generally been incapable of providing all the desired information at the desired analytical accuracy. Spectrometers are relatively high cost, complex, more difficult to implement and maintain than instruments, but have generally been able to provide the desired information.

As such, both classes of technology, as conventionally used, tend to offer poor value in applications such as alkylation catalyst analysis—instruments because they are inexpensive but do not offer comprehensive analysis; spectrometers because of the disproportionate expense to install and maintain, particularly their need for relatively complex sample conditioning systems capable of maintaining acid catalyst samples at a constant temperature. A desired analyzer for acid catalyst should approach or achieve the analytical performance of spectrometers and the comparatively low cost and simplicity of instruments. The above inventory of available instruments and analyzers therefore suggests a dilemma. But the instant inventor has discovered that the dilemma is a false one, the consequence of focusing on the analyzer rather than on the information required.

Analytical Problem

Rather than search for a single analyzer that will perform the required multi-component analysis, the instant inventor has identified the type of information needed to analyze acid catalyst online. This line of thinking led first to the observation that three channels of different or independent information are required. To understand this, consider the case of a univariate instrument whose measured response $R_1$ varies as a function of changing concentration of acid (A), hydrocarbon (H), and water (W). In a chemical system containing these three components with percent concentrations A, H, and W, an equation for $R_1$ can be written as follows:

$$R_1 = a_1 \cdot A + h_1 \cdot H + w_1 \cdot W \tag{1}$$

where $a_1$, $h_1$, and $w_1$ are the responsivities of the corresponding components in the mixture for the particular instrument. It is axiomatic that a single equation with three unknowns cannot be solved. This fact explains in mathematical terms why univariate instruments that measure density, refractive index, or conductivity have proven inadequate.

The inventor understood that what is needed to solve for A, H, and W is a system of three equations. One might conclude initially that two additional instruments would be required to provide responses required for two additional equations:

$$R_2 = a_2 \cdot A + h_2 \cdot H + w_2 \cdot W \quad (2)$$

$$R_3 = a_3 \cdot A + h_3 \cdot H + w_3 \cdot W \quad (3)$$

However, the instant inventor has recognized that the composition of acid catalyst is mathematically bounded because the concentrations of three components sum to 100%. This means that the chemical system only has two degrees of freedom, suggesting that its composition can be determined through addition of only one more instrument with a response $R_2$:

$$R_1 = a_1 \cdot A + h_1 \cdot H + w_1 \cdot W$$

$$R_2 = a_2 \cdot A + h_2 \cdot H + w_2 \cdot W$$

$$100 = A + H + W \quad (4)$$

If A, H, and W are known for a set of calibration samples, and if the instrument responses $R_1$ and $R_2$ are recorded for those samples, then the constants $a_i$, $h_i$, and $w_i$ can be determined. Subsequently, Equations (4) can be solved for A, H, and W by measuring $R_1$ and $R_2$ for an unknown sample.

Characteristics of the Analytical Solution

Equation (4) provides for the substantially complete determination of alkylation catalyst composition with a 2-channel analyzer provided two conditions are met. First, the responsivities $a_i$, $h_i$, and $w_i$ for A, H, and W, respectively, should be sufficiently different so that the solution to the Equation (4) is robust across the applicable range of concentrations for A, H, and W. Second, variation in the responses $R_1$ and $R_2$ depend substantially on variation in A, H, and W. If they do not, the implication would be that there is another degree of freedom caused by some chemical or physical effect, e.g., interactions between the components or temperature variation. However, as taught in the above analysis of the Analytical Problem, it has been found that this situation may be addressed by the addition of another instrument whose response uniquely relates to $R_1$, $R_2$, and the chemical or physical effect.

The nature of the measurement solution comes into clearer focus if water and dissolved hydrocarbons, including ASO, are viewed as solutes and HF or SA as a solvent. When changes in water concentration are relatively small, then, referring to Eq. (1), the term $w_1 \cdot W$ is relatively constant, in which case the chemical system has essentially a single one degree of freedom and Eq. (1) simplifies to $R_1 = h_1 \cdot H + C$. Rearranging to express H in terms of $R_1$ allows H to be measured straightforwardly as a function of density; viscosity; capacitance (a function of a material's dielectric constant); refractive index; absorption of electromagnetic radiation, e.g., microwave, infrared, near-infrared; and/or the emission of radio signals by the sample in a low magnetic field (low-field NMR). However, in practice the term $w_1 \cdot W$ in Equation (1) is non-zero and variable in magnitude, explaining why univariate measurement devices used alone have proven incapable of providing full characterization of alkylation catalysts.

Similarly, if the hydrocarbon fraction is constant, a device selective toward water in acid may have a response function across the concentration range relevant to acid catalysts. For example, referring to Equation (2), the Foxboro 871FT toroidal conductivity sensor is used routinely to measure low levels of water in HF with no dissolved hydrocarbons present, i.e., H=0 and the term $a_2 \cdot A$ is relatively constant. But in three-component acid catalyst systems the magnitude of the term $h_2 \cdot H$ is nonzero and both A and H are variable, with the consequence again that a single-channel instrument does not have a singular response.

Two Degrees of Freedom: Spectral Confirmation

Figure 2:
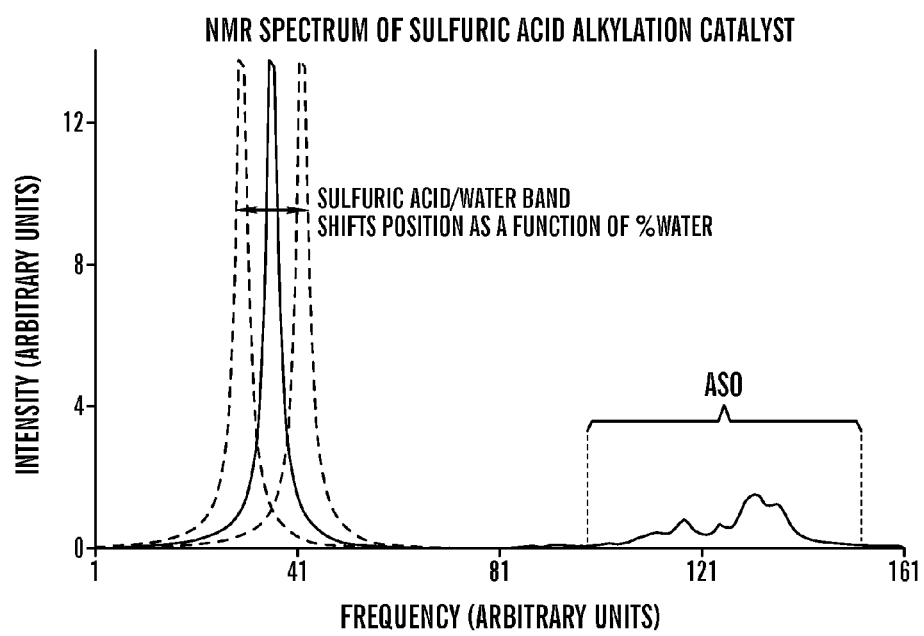
FIG. 2 is a plot of an NMR spectrum of Sulfuric Acid Alkylation Catalyst.

The NIR (Near Infrared) spectrum of HF catalyst (FIG. 1) and NMR (Nuclear Magnetic Resonance) spectrum of SA catalyst (FIG. 2) confirm the overall simplicity of the catalyst systems. As shown in FIG. 1, the NIR spectrum reveals three regions where the expressions of HF, hydrocarbon, and water are distinct if not fully resolved. While this makes direct measurement of intensities difficult, common data treatment and modeling techniques e.g., first derivatives and PLS (Partial Least Squares regression), respectively, permit direct correlation between spectral intensities and concentration. As shown in FIG. 2, the NMR analysis is actually less straightforward, as the spectrum shows only two major sets of peaks because water in SA does not exist as free water, but as a complex with SA. Therefore its concentration in the SA fraction is determined as a function of its effect on the position of the SA peak.

Figure 3:
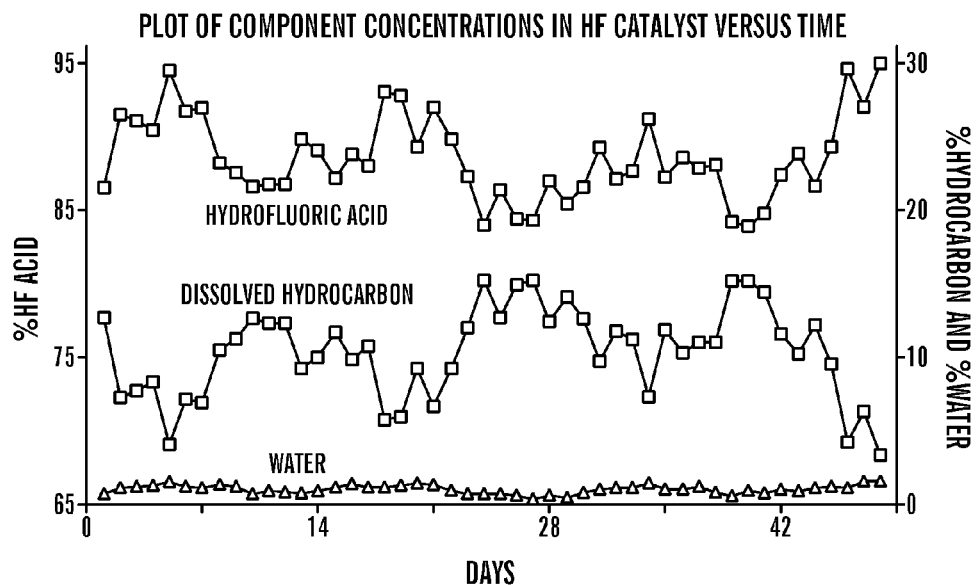
FIG. 3 is a plot of component concentrations in HF catalyst versus time.
Figure 4:
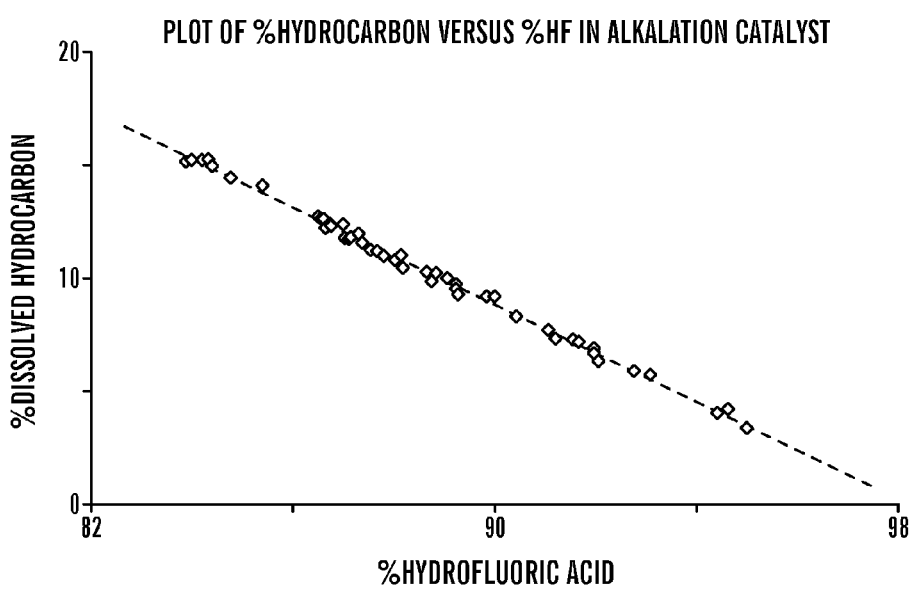
FIG. 4 is a plot of percent hydrocarbon versus percent HF in alkylation catalyst.

FIG. 3 shows that HF acid catalyst is a three-component system with two degrees of freedom: the amount of water is low and relatively constant while the concentrations of HF and ASO vary as near-perfect mirror images. FIG. 4 further emphasizes that for HF catalyst, the concentrations of acid and ASO relate in a nearly perfect linear fashion.

Hardware: Instruments and Sampling

Figure 5:
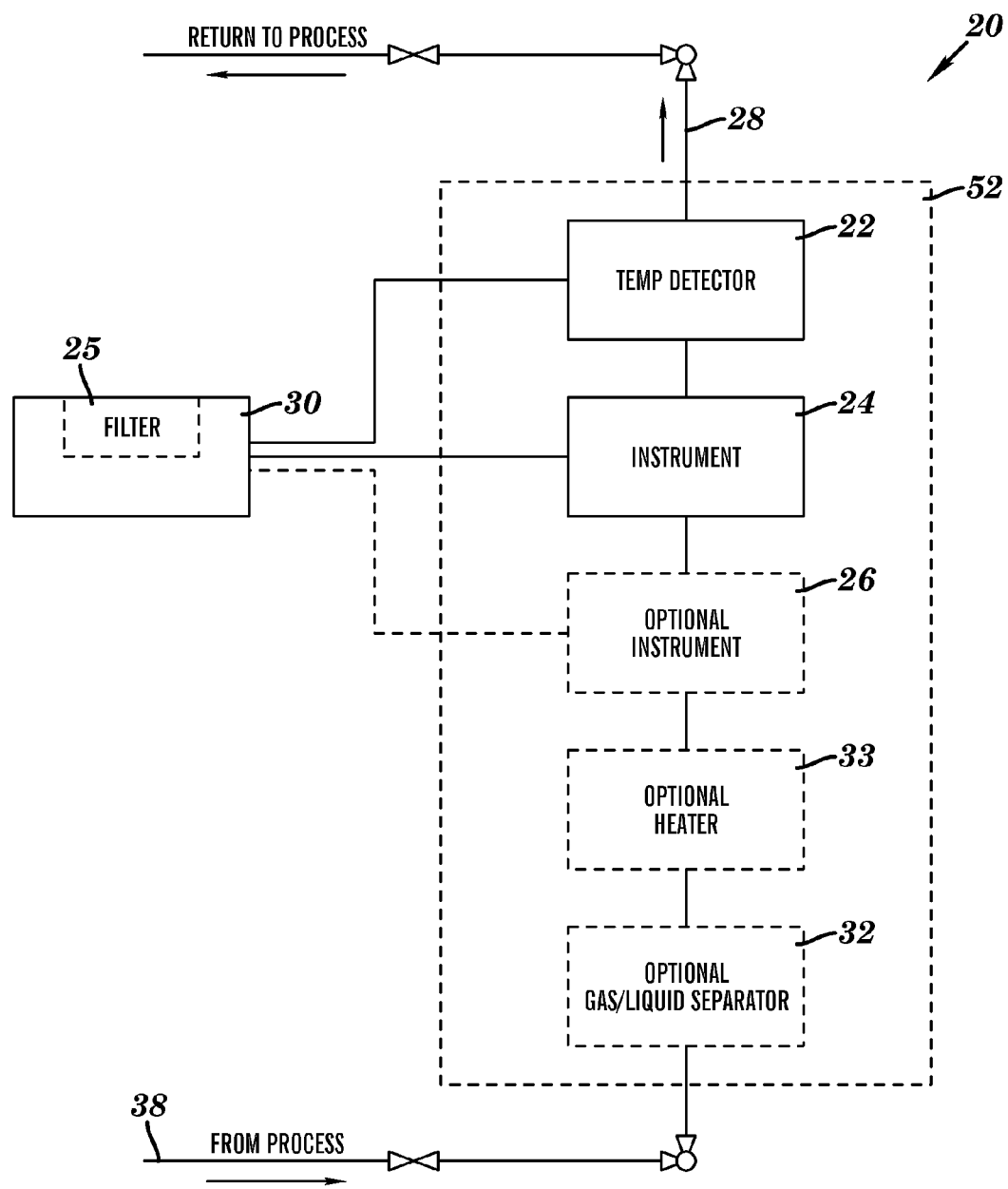
FIG. 5 is a schematic diagram of an embodiment of an acid catalyst analyzer of the present invention, with optional portions shown in phantom.

Turning now to FIG. 5, an embodiment of the present invention, referred to as an Acid Catalyst Analyzer, or ACA, 20, includes a temperature detector 22, an instrument 24, and optionally, one or more other instruments 26, disposed along a fluid flow path 28 as shown. ACA 20 also includes a (e.g., remote) data system (processor) 30 configured to capture and process signals from the temperature detector 22 and instruments 24, 26, etc., apply a model that interprets those signals, and the concentration of the catalyst, e.g., to a conventional alkylation unit control system (not shown).

It should recognized that in some embodiments, an ACA 20 having only a single instrument 24 may be used (e.g., in addition to temperature detector 22), such as for determining the on-line concentration of a single component in the alkylation catalyst mixture flowing through an alkylation process containing, i.e., an acid-soluble-oil (ASO), water, and HF or SA. In such a single-instrument embodiment, instrument 24 is configured to measure a property of the liquid mixture (e.g., acid catalyst) as it flows through fluid flow path 28. It is noted that the response of the particular instrument to concentration changes in one of the three constituents of the liquid mixture is substantially independent of the concentrations of the other constituents. In a particular exemplary embodiment, for example, instrument 24 may include a conductivity detector such as the aforementioned Foxboro 871FT conductivity detector. As discussed herein, it is recognized that conductivity is a response that is related to the concentration of water in the liquid mixture, and is substantially independent of the concentration of acid and ASO.

It should be recognized that instrument 24 may include any one of various other types, such as may be responsive to concentrations of either the acid (HF or SA), the acid-water fraction, or ASO. For example, instrument 24 may be a photometric sensor or photometer, including the above-referenced NIR, FTNIR (Fourier Transform NIR), Raman, and/or NMR spectrometers, and/or water-cut meters (e.g., the Red Eye® 2G Water-Cut Meter by Weatherford International, Ltd., Houston, Tex.). As still another option, instrument 24 may be a density measurement device, such as a Coriolis flowmeter (e.g., Foxboro CFS10 Coriolis flowmeter), which is responsive to changes in acid catalyst density caused by changes in hydrocarbon content. Use of such a density measurement device in a single-instrument embodiment has been shown to provide substantially accurate results for HF and/or SA in acid catalysts in the event the concentration of phase separated isobutane, IB/ps (liquid or gas) remains relatively constant over time. In the event the IB/ps tends to vary significantly, then a separator may be desired, as discussed with respect to the optional variation below.

The data generated by the single instrument 24 (e.g., conductivity detector or other single channel device) and temperature detector (e.g., RTD) 22 may then be used in combination with a model, by processor 30 to determine a temperature compensated concentration of the particular constituent of interest (which in this example is water). (It should be noted that while the temperature detector is shown and described as a device configured to explicitly determine temperature (e.g., an RTD or the like), temperature detector 22 may also include a device or data channel configured to enable implicit capture of temperature information, as will be discussed in greater detail hereinbelow.) Although not required, in particular embodiments, the output generated by processor 30 may be filtered (by optional filter 25) in a manner that would be familiar to those skilled in the art in light of the instant disclosure, such as to provide a smoother output plot of concentration over time, e.g., when IB/ps is present at levels that may cause instantaneous, random variation, giving the appearance of noise in a measured property of acid catalyst.

As mentioned above, in variations of the foregoing embodiments, it may be desirable to provide a second instrument. This second (optional) instrument 26 is configured to measure another property of the liquid mixture, so that the instruments 24 and 26 have mutually distinct responsivities to concentrations of the acid catalyst, ASO, and water. Processor 30 may then capture the data generated by the temperature detector 22 and both instruments 24, 26, and use the data in combination with the model to generate a temperature compensated concentration of the acid, the ASO, and water, in the liquid mixture. In particular embodiments, instrument 24 is a conductivity sensor and instrument 26 measures density.

Figure 6:
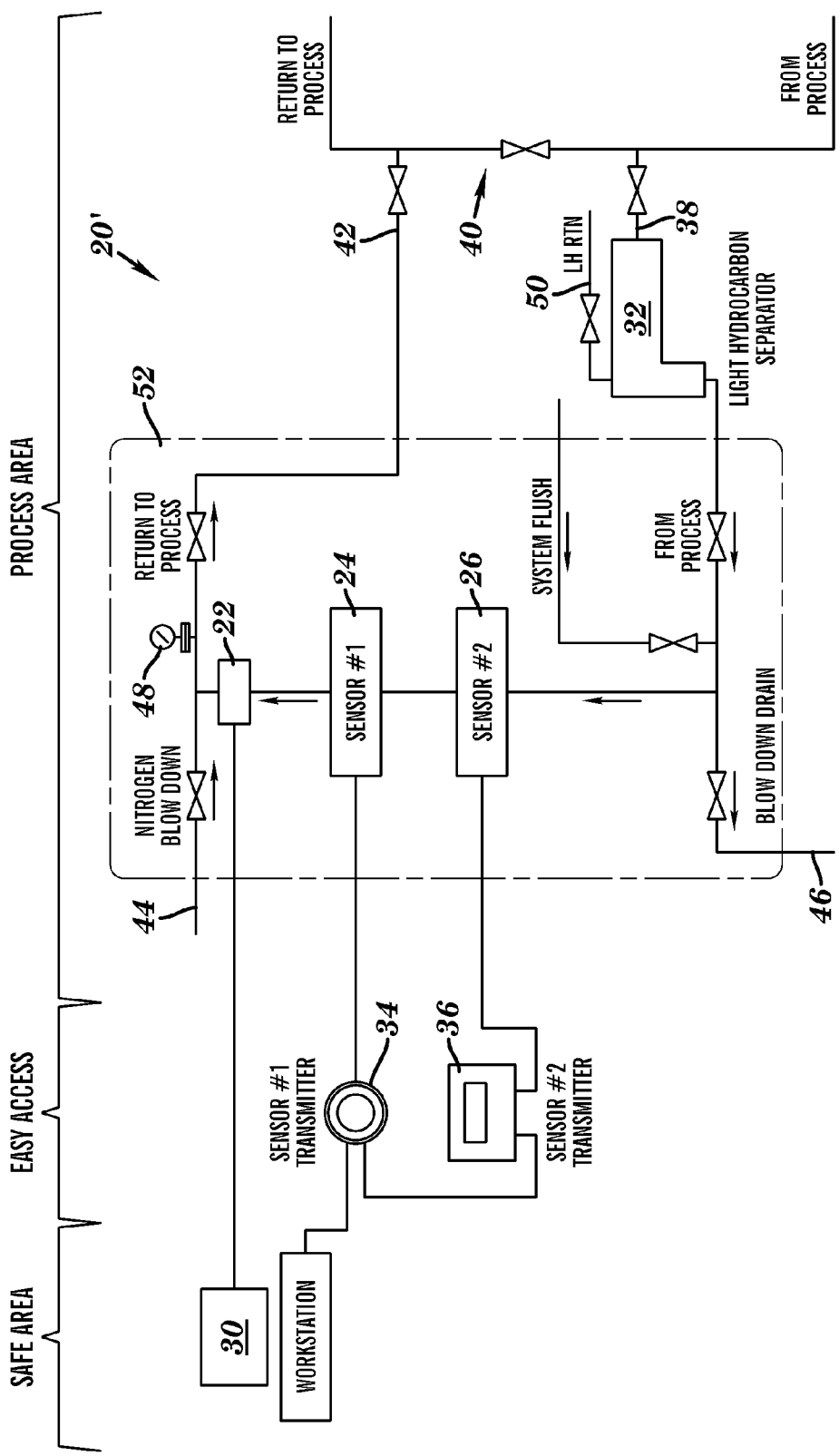
FIGS. 6 and 7 are views similar to that of FIG. 5, of optional embodiments of acid catalyst analyzers of the present invention.

As a further option, the foregoing embodiments may be provided with a separator 32 configured to remove hydrocarbon (e.g., IB/ps) present in a gas or liquid phase distinct from that of the liquid mixture (acid catalyst) sample stream, which otherwise behaves as a single phase. As shown, separator 32 may be disposed at or upstream of at least one or both of the instruments 24, 26, within fluid flow path 28. In particular embodiments, separator 32 is configured for continuous operation in a conventional manner, e.g., by passing liquid through to the fluid flow path 28, while returning lighter, phase-separated material through a suitable return line, such as shown in FIG. 6. Use of such a separator provides a continuous flow of liquid sample to the instrument(s) and temperature detector, to permit them to operate substantially continuously, i.e., without having to stop the flow of fluid prior to data capture. Alternatively, as will be discussed below with respect to FIG. 7, a separator may be incorporated into one or more of the instruments 24, 26, etc.

As a still further option, the various embodiments disclosed herein may be provided with a heater 33, such as a conventional inline heat exchanger shown schematically in FIG. 5. In particular embodiments, heater 33 may be used simply to help ensure that the liquid mixture entering the ACA from the process at 38 is maintained at or above a predetermined minimum temperature. For example, heater 33 may be particularly useful when the ACA is operated in winter conditions, such as to maintain the liquid mixture at a minimum level predetermined to help prevent dissolution (phase separation) of the liquid mixture during flow through fluid flow path 28. As also shown, it may be desirable to place heater 33 downstream of separator 32, so that IB/ps is removed prior to the application of heat. Heater 33 may also be useful to maintain sample in a temperature range where the response of instrument 24 or 26 to the change in a component concentration provides the required measurement resolution. For example, at water levels relevant to SA alkylation, the change in conductivity, C, as a function of the change of water concentration, W, i.e., dC/dW, is known to increase with temperature. Therefore, a heater 33 incorporated into ACA 20 may be used to heat the acid catalyst sample to a temperature sufficient to provide improved sensitivity to the changing concentration of water in SA without vaporizing light hydrocarbons present in the mixture, e.g., about 40° C. at typical process pressure.

In addition, although heater 33 may be conveniently disposed in line with fluid flow path 28 as shown, substantially any type of heater capable of maintaining the liquid mixture at or above the desired predetermined temperature may be used. For example, in the event the various components of the ACA are disposed within an optional cabinet 52, such as shown in phantom, heater 33 may be a conventional space heater configured to maintain the interior of the cabinet 52 at or above the desired minimum temperature.

It should be recognized that although heater 33 may be used to maintain the liquid mixture within flow path 28 within a predetermined temperature range, or above some minimum temperature, this is not required by the embodiments disclosed herein. Rather, as mentioned above, the present embodiments use one or more temperature detectors (or data channels) 22 in combination with a model at processor 30, in order to provide a temperature compensated output. Thus, these embodiments are configured to provide an output which is not dependent upon maintaining the liquid mixture at a particular temperature as it flows through flow path 28. Rather, these embodiments compensate for substantially any temperature of the liquid mixture, provided the temperature remains within a range predetermined to avoid dissolution at a low end, and excessive gasification, boiling, etc., at a high end.

Turning now to FIG. 6, in an alternate exemplary embodiment, ACA 20' instruments 24 and 26 are communicably coupled to one or more transmitters 34, 36, configured to capture data from the instruments and to transmit the data to a processor 30 such as a process controller or workstation as shown. In particular embodiments, transmitters 34, 36 may be single or multivariable transmitters of the type available commercially from Invensys Systems, Inc. As also shown, fluid flow path 28 of ACA 20' is communicably coupled at an upstream end 38 to an alkylation process 40. Fluid flow path 28 is returned to process 40 at a downstream 42 thereof.

The foregoing embodiments may also be provided with various additional aspects that would generally be known to those skilled in the art of fluid process control, such as a blow down inlet and outlet such as shown at 44 and 46, to facilitate cleaning of flow path 28, and a pressure sensor(s) 48 to monitor operating pressures. Also, as mentioned above, separator 32 includes a return 50 configured to return the IB/ps back to process 40, as shown.

Figure 7:
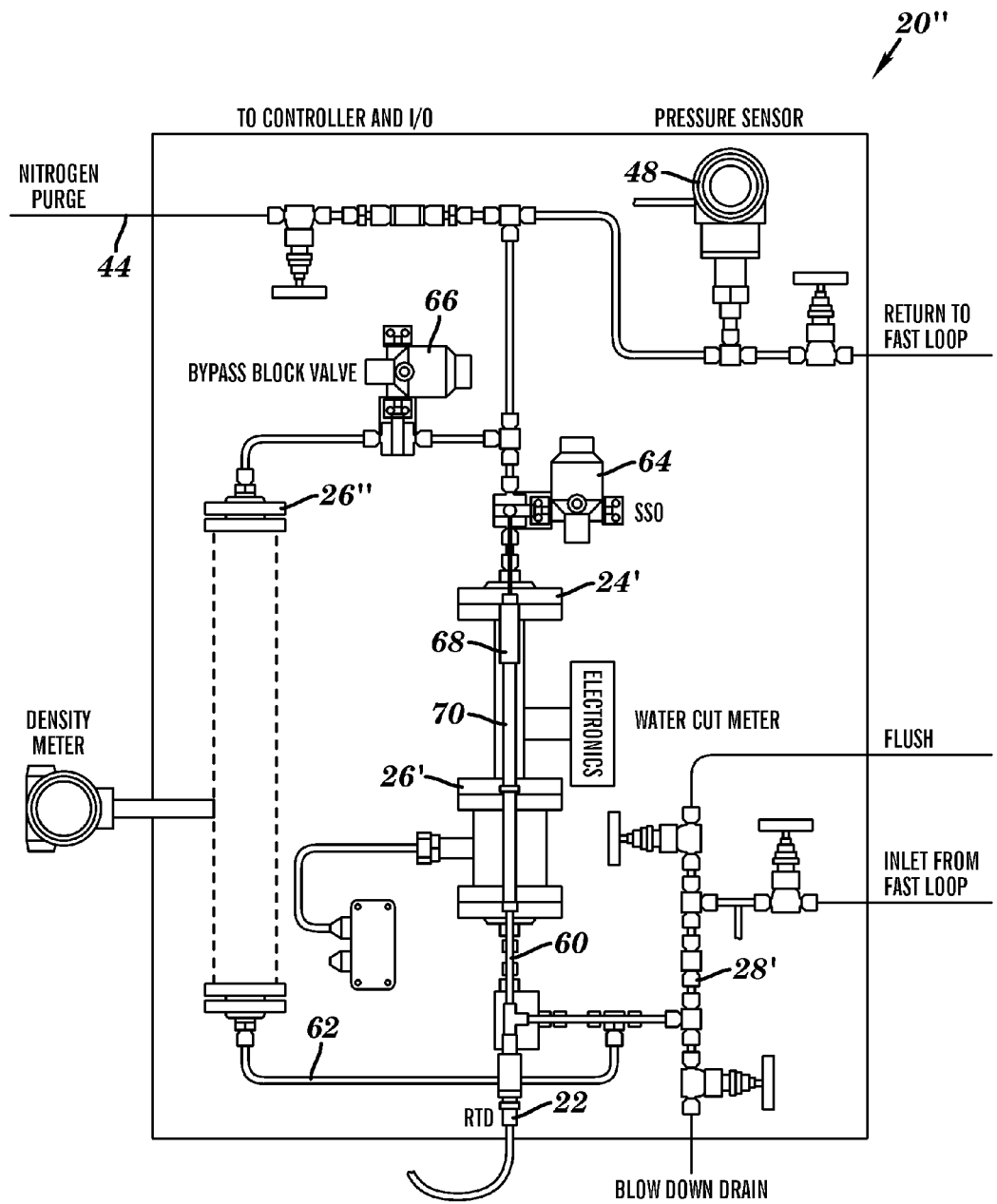

Turning now to FIG. 7, in yet another embodiment, an ACA 20" includes a fluid flow path 28' that includes parallel legs 60 and 62 that diverge from an upstream end of the flow path 28', and then reconverge at a downstream end of flow path 28'. The legs 60 and 62 each respectively include a bypass block valve 64 and 66. In this embodiment, the bypass block valves 64 and 66 are configured to periodically open and close in opposite synchronization with one another. This configuration thus periodically stops and starts the flow of the liquid mixture through each leg 60, 62, while the aggregated liquid mixture (i.e., upstream and downstream of the legs) flows substantially continuously.

As also shown, this embodiment enables the use of an instrument 24', having an integral separator that removes hydrocarbon (e.g., IB/ps) present in a gas or liquid phase distinct from that of the liquid mixture (acid catalyst) sample. This integral separator may thus take advantage of the alternating start/stop fluid flow through leg 60, to effectively provide a self-separation of IB/ps from the acid catalyst sample while flow through leg 60 is stopped. In this regard, the bypass block valve 64 can be configured to stop the fluid flow through leg 60 for long enough to permit the IB/ps to separate from the acid catalyst sample and accumulate within cavity 68 of instrument 24'. The instrument 24' may then capture data from the acid catalyst 70 (e.g., which collects at a lower portion of cavity 68), before valve 64 opens to re-start fluid flow. The data provided by instrument 24' may be combined with temperature data from RTD 22 and a model at processor 30 (FIG. 5) as discussed above with respect to ACA 20, to generate concentration values for at least one of the constituents of the alkylation process.

In a particular non-limiting example, instrument 24' may include a water cut meter, such as the EASZ-1 meter loop powered water cut meter (EESiFlo® North America, Mechanicsburg, Pa. USA), which has been modified in accordance with the teachings of the present invention to include an integral separator in the form of a cavity 68 sized and shaped to enable quantitative accumulation of the aforementioned IB/ps. This ACA 20" thus provides for convenient removal of IB/ps that may otherwise interfere with property measurement of the liquid mixture using a single instrument 24', while providing for a temperature compensated determination of a concentration of at least one of the constituents of the acid catalyst.

In a variation of the foregoing embodiment, one or more optional instruments 26', 26" may also be used along fluid flow path 28'. For example, an optional instrument 26' may be located in series with instrument 24', e.g., within leg 60, or alternatively may be disposed in parallel with instrument 24', e.g., as shown at 26" in phantom on leg 62. As a non-limiting example, instrument 26' may include a Foxboro 871FT toroidal conductivity sensor, while instrument 26" may include a density meter such as the Sarasota™ density meter (Thermo Fisher Scientific, Inc., Sugar Land, Tex.). It should be recognized, however, that substantially any instrument capable of measuring a property of one or more of the constituents of the liquid mixture as discussed hereinabove, may be used while remaining within the scope of the present invention. It should also be recognized that although embodiments have been shown and described herein as having one or two instruments in addition to a temperature detector, substantially any number (N) of instruments may be provided without departing from the scope of the present invention.

Note that the embodiment of FIG. 6 is similar to that of FIG. 5, while having some additional aspects that may be desirable in some applications, such as to facilitate maintenance thereof. For example, isobutane or hot alkylate may be used to flush HF from the sample flow path, followed by nitrogen blow down to drain for a final purge, in a manner that will be familiar to those skilled in the art, in view of the instant disclosure.

Optional aspects applicable to substantially any of the embodiments discussed herein may also include, but are not limited to, the following:

Sample shut-off valves to isolate the analyzer system from the sample fast loop;

Inlets (and outlets) for ($IC_4$) and nitrogen to purge the system for maintenance following closure of the shut-off valves;

Appropriate metallurgy used throughout (e.g., Hastelloy may be preferred in particular applications, although "Carpenter 20" alloy may be used for SA service, and low-carbon steel may be employed for some components used in HF service);

A layout such that sample flows from bottom to top so as to displace sample in the direction that IB/ps tends to migrate while purging to drain with nitrogen is done from top to bottom in a fashion consistent with liquid flow under gravity;

The system layout should eliminate "low spots" and "hiding places" where acid can persist during/after purging;

A continuous-flow separator 32 to remove IB/ps from the sample stream, without which inhomogeneous sample flowing through sensors could cause erratic responses, as discussed above;

Optional sample shutoff (SSO) valves (also referred to as Bypass Block Valves) 64, 66 (FIG. 7) to automatically stop sample flow at a fixed interval, e.g., as programmed into the ACA controller 30 (employed as an alternative strategy for eliminating erratic sensor responses caused by IB/ps) to allow IB/ps to float upward and away from the sensor(s), yielding a single-phase sample);

An optional enclosure, such as shown schematically at 52 of FIGS. 5, 6, to protect ACA components from the elements, e.g., with air purge and an HF gas sensor on the outlet (when measuring HF catalyst);

An optional enclosure and/or heater for use when ambient temperatures may undesirably cool the liquid mixture as discussed hereinabove;

A flow controller, perhaps as simple as an orifice;

A pressure sensor 48 (FIGS. 6, 7); and

A temperature sensor (or data channel) 22 in the form of a stand-alone device, one that is integrated into any one or more of the instruments 24, 26, etc., or in the form of a data channel of a multi-channel device, used to explicitly or implicitly generate temperature information for the liquid mixture.

The following is a non-limiting list of exemplary sensors and properties measured, which may be used in particular embodiments of the present invention:

a. Foxboro 871FT (Invensys®) conductivity meter;

b. Foxboro CFS10 (Invensys®) coriolis flow meter (density and temperature; flow is also monitored to provide information about analyzer operation but is not used in the calculation of acid composition);

c. Agar Corporation OW-301 water cut meter (microwave);

d. Eesiflo International EASZ1 water monitor (dielectric);

e. K-Patents PR-01-S process refractometer; and f. Low-field NMR, i.e., proton resonance frequency<50 MHz.

As discussed herein, instruments 24, 24', 26, 26', etc., (and temperature detector 22) have been described in various embodiments as single channel, stand-alone devices. However, it should be recognized that these various instruments and temperature detector may include devices of substantially any type, including multi-channel devices, provided they have one or more data channels which are responsive to concentrations of any one or more constituents of the liquid mixture (e.g., of the acid (HF or SA), the acid-water fraction, and/or ASO) as described herein. For example, multi-channel devices such as the above-referenced NIR, FTNIR (Fourier Transform NIR), NMR, and/or Raman spectrometers, may be used as one or more of the devices 22, 24, 24', 26, 26', etc.

For example, with reference back to FIG. 5, in particular embodiments, temperature detector 22 and instrument 24 may take the form of a single multi-channel (e.g., NIR) spectrometer. A gas/liquid separator 32 may be disposed in series with the NIR spectrometer to enable substantially continuous sample flow through flow channel 28 as discussed above. (Similarly, with reference to FIG. 7, temperature detector 22, instrument 24', and/or instrument 26' may take the form of a single multi-channel spectrometer modified to include an integral separator in a parallel flow path arrangement as also shown and described hereinabove.) One channel of the spectrometer may thus be configured to serve as detector 22 to generate temperature information for the liquid mixture, while another channel may serve as instrument 24, 24', etc., to generate information corresponding to concentration of one of the components of the liquid mixture as discussed hereinabove. In a variation of this approach, a third channel of the NIR spectrometer may be used to generate information as described hereinabove with respect to instrument 26, 26', etc.

Moreover, rather than generating temperature information directly, channel 22 of the spectrometer may be used to generate data corresponding to another aspect of the liquid mixture, so that multiple (e.g., three or more) channels of the spectrometer may be used to gather sufficient information to effectively infer the temperature of the liquid mixture, as described in greater detail hereinbelow. In this manner, the need for directly determining the temperature of the liquid mixture is obviated, e.g., so that channel 22 may be used to gather other useful information. Thus to summarize this example, three channels of the spectrometer correspond to devices 22, 24, and 26, with channel 22 used either for direct (explicit), or indirect (inferential) temperature measurement using the model, as discussed in greater detail hereinbelow.
Improvements Over Standard Implementations of NIR and NMR At least three features of the embodiments discussed herein, or practices associated with their implementation, represent significant improvements over established approaches to acid catalyst analysis based on conventional NMR and NIR spectroscopy. First, in particular embodiments, separator 32 (FIGS. 5, 6), removes IB/ps, which permits substantially real-time analysis of continuously flowing sample as discussed hereinabove. In alternate embodiments, such as shown and described hereinabove with respect to FIG. 7, a separator may be incorporated within an instrument such as at 24', which, in combination with use of a flow path having parallel legs 60, 62, also enables the continuous flow of liquid mixture (e.g., acid catalyst sample). This contrasts with conventional NMR and NIR approaches, which generally require a stationary sample, i.e., periodic, frequent stop-flow to ensure that any IB/ps floats up and clears the sample probe or transmission cell, respectively, where analysis takes place. This incorporation of a separator into the sample flow path thus provides for substantially real-time and continuous sample analysis.

Second, property predictions by the embodiments of the ACA discussed herein are substantially insensitive to variation in sample temperature because responses from a plurality of channels are used to make property models in which temperature is an implicit or explicit variable. Models incorporating responses of instruments 22, 24, 24', 26, 26', etc., whose purpose is to follow changes in composition, e.g., the CFS10 (total hydrocarbon) and the 871FT (water), may be used to compensate for temperature implicitly or explicitly, obviating the requirement for sampling systems that ensure presentation of an isothermal sample for analysis.

The apparent simplicity of NIR and NMR spectra belies the complexity of such sample conditioning systems, which may cost up to twice as much as the base spectrometer. The current state of the art in process NMR depends on an isothermal sample. Though not the case with NIR spectroscopy generally, the established approach to NIR analysis of acid catalyst is decidedly isothermal because the property models are isothermal, and samples' spectral responses vary significantly as a function of temperature. Embodiments of the present invention may thus utilize an NIR spectrometer without the need for an isothermal sample, such as by use of NIR models developed as described herein, to compensate for sample temperature implicitly (e.g., inferentially) or explicitly. Embodiments including such a model, in combination with a separator to remove phase-separated isobutane, may dramatically reduce the cost to install and maintain an NIR analyzer system relative to the prior art.

Figure 8:
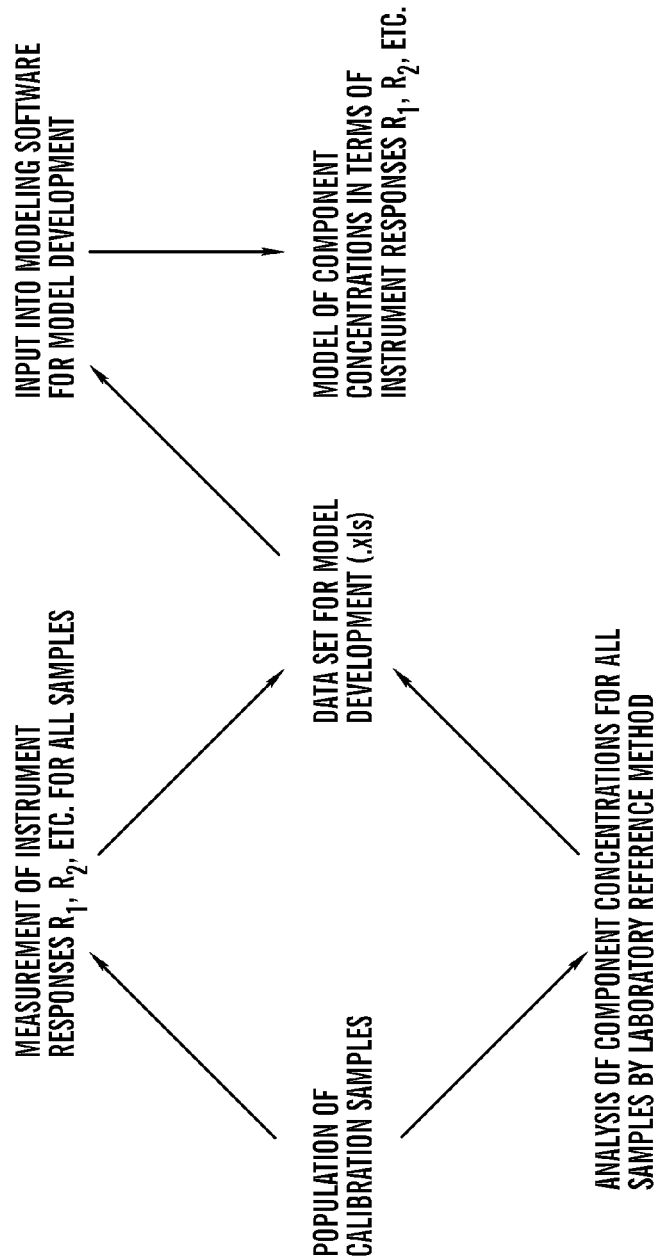
FIG. 8 is a flow diagram showing calibration of embodiments of the present invention.

Third, instruments 24, 24', 26, 26', etc., (and detectors 22) used in various embodiments of the ACA have core technology that is relatively simple, robust, simple to install, and easy to commission. Installation and commissioning of conventional NIR and NMR systems, including their temperature conditioning approaches, can take weeks. By contrast, the ACA 20, 20', 20'', etc., has relatively simple installation requirements, while commissioning may typically be completed within two days. Perhaps even more significant, the combined mean-time-before-failure of representative instruments 24 and 26, such as the Invensys® CFS10 conductivity meter and the Invensys® 871FT Coriolis flowmeter is estimated to be more than 29 years.
Calibration: Modeling Concentration in Terms of Instrument Responses As discussed hereinabove in a previous section (Analytical Problem), aspects of the present invention include a two-step process for obtaining concentration values for components in acid catalyst based on instrument responses $R_1$ and $R_2$. In general terms, a property P is predicted by applying $\text{MODEL}_P$ to responses measured on that sample:

$$P = \text{MODEL}_P \cdot [R_1, R_2, R_3, \ldots, R_N] \quad (5)$$

where the responses $R_1, R_2, R_3, \ldots, R_N$ may be measured on N different single-channel instruments, or on a single N-channel spectrometer. FIG. 8 shows the process in terms of data collected as depicted in Table 2 for the three-channel case, and then analyzed to create a model, which is then applied to the responses $R_1, R_2, R_3, \ldots, R_N$ measured by the instruments for a sample of unknown composition.

TABLE 2

Example of a calibration data set for a 3-channel analyzer system

| SAMPLE INFORMATION | | CHANNEL RESPONSES | | | PROPERTY VALUES (LAB OR ONLINE) | | |
|---|---|---|---|---|---|---|---|
| Lab ID | Date/Time | Ch. 1 | Ch. 2 | Ch. 3 | % Acid | % Hydrocarbon | % Water |
| 1 | Day 1 | $R_{11}$ | $R_{21}$ | $R_{31}$ | $A_1$ | $H_1$ | $W_1$ |
| 2 | Day 2 | $R_{12}$ | $R_{22}$ | $R_{32}$ | $A_2$ | $H_2$ | $W_2$ |
| 3 | Day 3 | $R_{13}$ | $R_{23}$ | $R_{33}$ | $A_3$ | $H_3$ | $W_3$ |
| . | . | . | . | . | . | . | . |
| . | . | . | . | . | . | . | . |
| . | . | . | . | . | . | . | . |
| n | Day n | $R_{1n}$ | $R_{2n}$ | $R_{3n}$ | $A_n$ | $H_n$ | $W_n$ |

As used herein, the term "modeling" refers to the process of mathematically relating responses obtained from a plurality of response channels to the known chemical composition of calibration samples, the result being a "model." As used herein, the term "model" is not limited in form to a system of linear equations such as depicted in Equations (4) or (5), nor is it limited to use of responses $R_1$, $R_2$ from only two instruments. Rather, "model" refers to any equation or a system of equations, which may include multiple terms for variables (parameters) measured by the embodiments shown and described herein, and which alone or in combination predict one or more of the component properties (concentrations) of interest.

Calibration: Explicit and Implicit Temperature Compensation

Furthermore, models may be developed so as to be capable of accurately predicting properties even when variation in sample temperature has a direct effect on one or more inputs $R_i$ apart from e.g., a component concentration change. Referring to Equations (1), (2), and (3), this would mean that one or more values $d(a_i)/dT$, $d(h_i)/dT$, and $d(w_i)/dT$ are nonzero. In one approach, predictions can be made insensitive to temperature by employing responses $R_i$ from three or more single-channel instruments, or from an N-channel spectrometer (N≥3). If Equation (4) is understood to apply under isothermal conditions (dT=0), then Equation (6) illustrates the addition of a third device to deal implicitly with the additional degree of freedom resulting from temperature variation (the boundary condition A+H+W=100 still applies):

$$R_1 = a_1 \cdot A + h_1 \cdot H + w_1 \cdot W$$

$$R_2 = a_2 \cdot A + h_2 \cdot H + w_2 \cdot W$$

$$R_3 = a_3 \cdot A + h_3 \cdot H + w_3 \cdot W \quad (6)$$

Provided that $R_1$, $R_2$, and $R_3$ relate substantially uniquely to T, and adequate variation exists among all coefficients $a_i$, $h_i$, or $w_i$, a suitable multivariable modeling method such as PLS, can be used to obtain models that provide predictions for A, H, and W as depicted in Equation (5), which are substantially insensitive to temperature variation. This can be termed passive or implicit temperature compensation.

In explicit or active temperature compensation, models are developed which incorporate temperature as a measured variable. Equation (7) is an alternative way to express the relationship between the concentrations of interest and measured responses, with temperature (T) being an explicit variable (the boundary condition applying still):

$$A = a'_1 \cdot R_1 + a'_2 \cdot R_2 + t_A \cdot T$$

$$H = h'_1 \cdot R_1 + h'_2 \cdot R_2 + t_H \cdot T$$

$$W = w'_1 \cdot R_1 + w'_2 \cdot R_2 + t_W \cdot T \quad (7)$$

where T, $t_A$, $t_H$, and $t_W$ have been substituted for $R_3$, $a'_3$, $h'_3$, and $w'_3$, respectively. Thus, whether models incorporate temperature implicitly or explicitly, the development of N property models for a determined system where A+H+W=100 requires a minimum of N measured parameters.

Calibration: Characteristics of the Data Set

At least three observations about samples and property values should be noted concerning the calibration sample set and the calibration process.

Concentration Ranges. In particular embodiments, the sample set should include samples whose composition spans the full range of relevant property values that the process will exhibit and the analyzer will be required to analyze.

Sample Composition. To the extent practical, the sample set in particular embodiments should also have all possible combinations of component concentrations.

Temperature Range. When the goal is to develop models that provide substantially accurate predictions when temperature varies, calibration samples should generally span the full range of temperatures of interest manner that is not correlated with composition.

Data Modeling. Calibration involves the statistical reduction of data for a population of samples. Accordingly, multivariable statistical modeling methods such as MLR (multiple linear regression) or PLS (partial least squares), and/or other modeling methods known to those skilled in the art may be used.

Additional Considerations Related to Representative Implementation

The following are practices related to the implementation of various embodiments of the ACA.

Calibration of Sensors

The above-referenced CFS10 conductivity, the 871FT coriolis flowmeter, or any other sensor used in the ACA embodiments hereof will not be required to report percent acid, percent water, or percent organic (e.g., ASO) directly. Instead, the "raw" responses from the instrument will be used both for the creation of property models and for routine composition prediction using those models. Thus, signals from the instruments are gathered into a common data handling device (e.g., processor 30) where models are applied to predict percent (%) acid, percent (%) hydrocarbon, and percent (%) water.

Generation of Reference Values for Modeling

The property (lab) values noted may come from a variety of sources. A traditional analysis approach may be used, which includes obtaining samples and testing them in the laboratory by a conventional (e.g., manual) test method. Alternatively, for development purposes, it may be possible to use data captured from current installations that employ spectrometric analyzers. These data may be used to calibrate embodiments of the present invention.

Temperature as an Analytical Variable

As mentioned hereinabove, conventional process spectrometer systems employed for the analysis of acid catalyst, i.e., NIR (HF) and NMR (SA) commonly are designed to control sample temperature. It has been generally understood that such control was required in order ensure reproducibility of samples' spectral response, which are known generally to exhibit variation as a function of temperature. Similarly, as also mentioned above, the various devices incorporated into embodiments of the present invention may also have some temperature dependency. As such, it should be recognized that the embodiments hereof may also include such conventional sample temperature control.

However, as also discussed above, particular embodiments of the present invention avoid the need for such temperature control by providing for temperature compensation. This temperature compensation may be provided by capturing the temperature either explicitly or implicitly. For example, temperature may be captured explicitly using temperature detector 22 (FIGS. 5-7), and/or by using temperature capture/compensation technology commonly incorporated into various instruments 24, 26, etc. (In this regard, for example, in addition to flow and density, the above-referenced CFS10 conductivity meter also reports sample temperature.) Embodiments of the present invention may thus include temperature as a measured variable (e.g., a data channel) via stand-alone temperature detector 22. This temperature information may then be used with the aforementioned data model, to compensate for temperature-dependent changes in responses/data provided by the other instruments (e.g., the other data channels).

Alternatively, as also discussed above, sample temperature may be captured implicitly, such as by providing a sufficient number of substantially mutually distinct data channels (e.g., three or more for the acid catalysts described hereinabove) provided by various instruments used in combination, and/or by the use of multi-channel devices such as the aforementioned spectrometers.

Regardless of which of these approaches are used, the various embodiments of the present invention may use this direct or inferred temperature information to compensate for the particular temperature of the liquid mixture, to reduce or substantially eliminate the requirement for sample conditioning (i.e., isothermal temperature control) such as commonly used with spectrometric analyzers.

Validation

Figure 9:
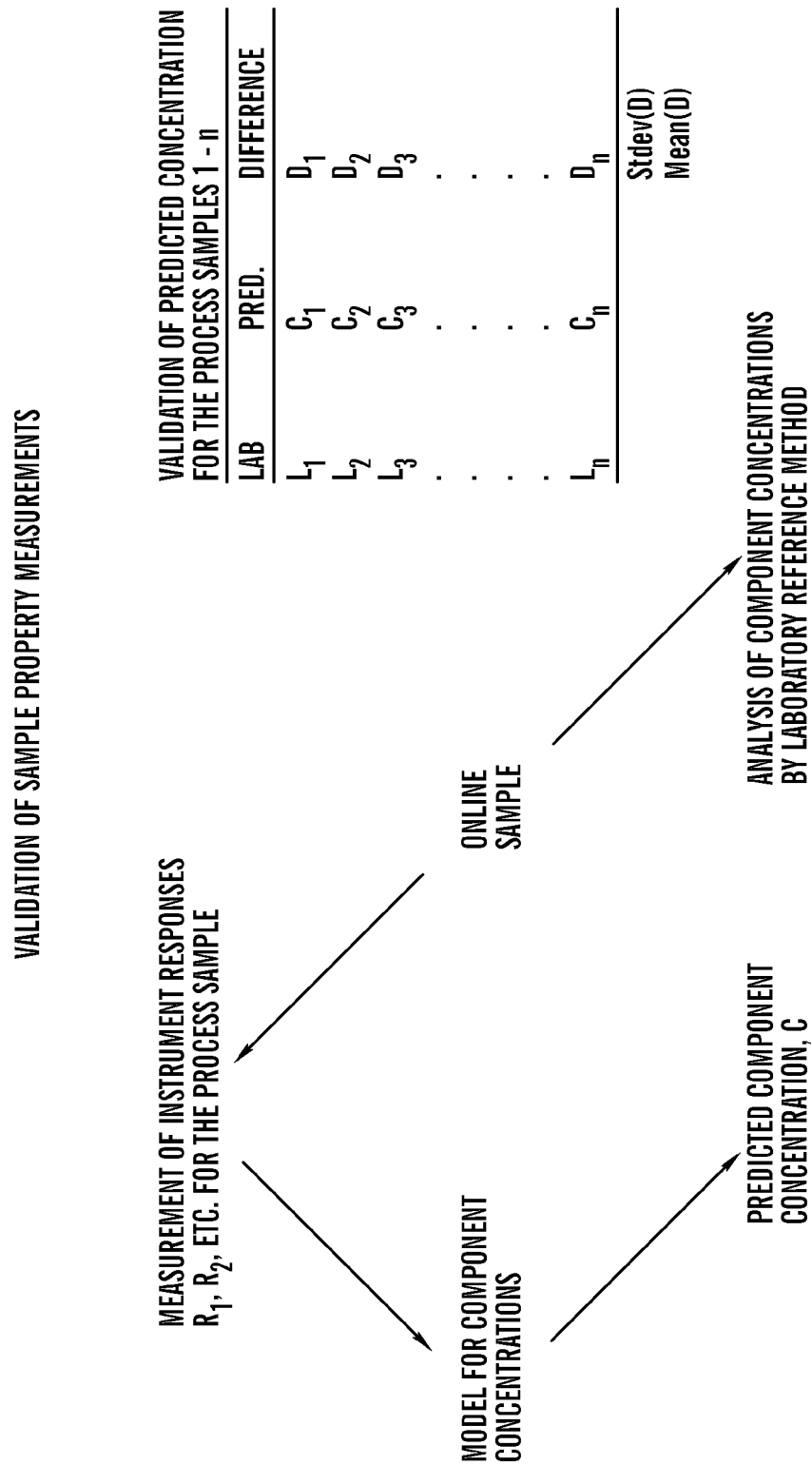
FIG. 9 is a flow diagram showing validation of property measurements generated by embodiments of the present invention.

After modeling, the accuracy of predictions made by the ACA 20, 20', 20", etc., with the model may be validated through the process depicted in FIG. 9.

The standard deviation on the difference between Lab and Predicted values, Stdev(D), is sometimes referred to as SEP (Standard Error of Prediction) or RMSEP (root mean square error of prediction). SEP is simply a measure of agreement between the Lab and Predicted values. Insofar as both the predicted values and the Lab values have associated uncertainties, the name SEP implies inappropriately that the differences are due to errors in the predicted values only, whereas reference values invariably have associated errors and therefore may be referred to simply as SE (standard error).

G. Additional Considerations

ReVAP and Alkad Additive Systems

HF Alkylation

The analytical problem may become more complex if yet another component (e.g., an additive such as ReVAP or Alkad) is added into the catalyst to reduce HF volatility. However, direct determination of the additive in the in-process catalyst may not be necessary or beneficial, as other streams typically exist within the (e.g., alkylation) unit whose composition may be easier to measure, but which do not contain one of the other components, e.g., ASO.

Alternative Applications

Embodiments of the present invention have been shown and described herein as particularly useful in alkylation processes, e.g., due to the benefits of higher accuracy relative to solitary instruments, and lower price and ease of use vs general purpose spectrometric analyzers. However, it should be recognized that these embodiments more broadly provide a multi-channel multi-variable analyzer, e.g., by the integration of two or more disparate instruments into a system, and/or by the use of temperature compensation rather than temperature conditioning, that provides many of the benefits of a multi-channel spectrometer in a generally simpler, more robust, and cost effective manner, which may lend itself to creation and application of models using techniques similar to those applied in quantitative spectrometry.

An example of another application that may benefit from embodiments of the present invention may include one that is related to operation of HF alkylation units. This application concerns control of an HF regeneration tower (a distillation unit that pushes high-purity HF overhead and leaves water and polymer/ASO at the bottom in the form of a residue for disposal). The objective of this distillation unit is to remove as much HF out of the residue as possible to minimize the need for caustic materials to neutralize any remaining HF in the residue prior to disposal (e.g., incineration).

The residue may thus be pumped through the embodiments of, for example, FIGS. 5 and 6, to measure percent (%) organic, percent (%) HF, and percent (%) water. In this manner, operation of the distillation unit may be continued until the percent (%) HF reaches a sufficiently low level.

Having described various embodiments of the present invention, exemplary methods of operation will now be described in connection with the following Tables 3 and 4.

Referring to Table 3, an exemplary method is provided for on-line concentration determination of at least one component in a liquid mixture, which is an acid catalyst for hydrocarbon conversion containing unknown concentrations of, an acid (HF or SA), an acid-soluble-oil (ASO), and water. The method includes supplying 100 the liquid mixture to an instrument configured to have responsivities to concentrations of one of the acid, ASO, and water, independently of the concentrations of the others of the acid catalyst, ASO, and water. The liquid mixture is supplied 102 to a temperature detector. A property of the liquid mixture is measured at 104, and temperature data is generated at 106. Property and temperature data is captured at 108, and a processor uses the data and a model of responsivities to various concentrations of the acid, ASO, and water at various temperatures, to determine 110 a temperature compensated concentration of at least one of said acid, ASO and water, in the liquid mixture.

TABLE 3

- 100 supplying the liquid mixture to an instrument;
- 102 supplying the liquid mixture to a temperature detector;
- 104 measuring a property of the liquid mixture using the instrument;
- 106 generating temperature data for the liquid mixture using the temperature detector;
- 108 capturing, with a processor, data generated by the instrument and temperature detector;
- 110 determining, with the processor, using the data in combination with a model, a temperature compensated concentration of at least one of the acid, ASO, and water.

Optional aspects of the foregoing method are described in connection with Table 4. As shown, the temperature compensated concentration is filtered at 112. A conductivity measurement device is optionally used as the instrument at 114. At 116, the liquid mixture is optionally supplied to an other instrument, in which the instruments are configured to have mutually distinct responsivities to concentrations of the acid, ASO, and water, and both instruments are used by the processor to determine temperature compensated concentration of at least two constituents of the liquid mixture. A density measurement device is optionally used as the other instrument at 118. Hydrocarbons separated from the bulk acid catalyst as a distinct phase (liquid or gas) are optionally removed 120 from liquid sample mixture prior to using the instrument for property analysis, optionally while the liquid mixture is conveyed substantially continuously in a downstream direction. Optionally, at 121, the instruments and temperature detector are configured as a multi-channel spectrometer, having at least three channels, e.g., for generating information corresponding to three mutually distinct parameters of the liquid mixture, for explicit or inferential temperature detection of the liquid mixture. The separating is effected using an alternating stop flow via parallel flow paths at 122. The liquid mixture is obtained from an acid catalyst stream in a hydrocarbon conversion process, including either HF or SA at 124. A model is used at 126 which includes a model data set of expected outputs from the instruments under a plurality of known concentrations of acid, ASO, and water.

which may be used to compensate for temperature variation in the case where the sampling system is not designed to control sample temperature. Alternatively, the sampling system does not actively control sample temperature, but instead a calibration data set such as that described in Table 2 is acquired across a wide range of temperatures $T_n$ such that the effect of temperature on responses $R_1, R_2, R_3, \ldots, R_n$ is represented in the calibration data set across a range of relevant temperatures to permit acid, ASO, and water to be modeled without direct application of a correction for measured temperature.

It should also be recognized that although the various embodiments hereof have been shown and described as suitable for online use, e.g., by direct connection to an alkylation process, these embodiments may also be used in an offline mode without departing from the scope of the present invention.

It should be noted that the various modules and other components of the embodiments discussed hereinabove, including processor 30, may be configured as hardware, as computer readable code stored in any suitable computer usable medium, such as ROM, RAM, flash memory, phase-change memory, magnetic disks, etc., and/or as combinations thereof, without departing from the scope of the present invention.

It should be understood that any of the features described with respect to one of the embodiments described herein may be similarly applied to any of the other embodiments described herein without departing from the scope of the present invention.

TABLE 4

- 112 temperature compensated concentration is filtered
- 114 Instrument is conductivity measurement device
- 116 liquid mixture is optionally supplied to an other instrument
- 118 Other instrument is density measurement device
- 120 Phase-separated hydrocarbons optionally separated from liquid mixture prior to using the instrument(s), optionally while the liquid mixture is conveyed substantially continuously downstream
- 121 Optionally, the instruments and temperature detector are configured in the form of a multi-channel spectrometer, having at least three channels, e.g., configured for generating information corresponding to three mutually distinct parameters of the liquid mixture, for explicit or inferential temperature detection of the liquid mixture.
- 122 separating effected using alternating stop flow via parallel flow paths
- 124 liquid mixture obtained from an HF or SA acid catalyst stream in a hydrocarbon conversion process
- 126 Model used includes model data set of expected outputs from the instruments under a plurality of known concentrations of acid, ASO, and water It should be recognized that in the foregoing embodiments, instruments 24, 24' 26, and 26', etc., may be incorporated into a single device, provided they have mutually distinct responsivities to concentrations of the acid catalyst, ASO, and water. So for example, these instruments may include a single NMR or NIR spectrometer capable of detecting multiple responses to one or more stimuli, and whose sampling system is configured with a sensor to measure the sample temperature, In the preceding specification, the invention has been described with reference to specific exemplary embodiments for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

Having thus described the invention, what is claimed is:

1. An apparatus for on-line concentration determination of at least one component in a liquid mixture flowing through an alkylation process, which liquid mixture is an acid catalyst for hydrocarbon conversion containing an unknown concentration of an acid, an acid-soluble-oil (ASO), and water, said apparatus comprising: an instrument configured for measuring a property of the liquid mixture; the instrument configured to have responsivities to concentrations of one of the acid, ASO, and water, substantially independent of the concentrations of the others of the acid catalyst, ASO, and water; an other instrument configured for measuring another property of the liquid mixture; the instruments configured to have mutually distinct responsivities to concentrations of the acid, ASO, and water; a temperature detector configured to generate temperature data for the liquid mixture; a model of responsivities to various concentrations of the acid, ASO, and water at various temperatures; a processor configured to capture data generated by the temperature detector and the instruments, and to use the data in combination with said model to determine a temperature compensated concentration of said one of the acid catalyst, said ASO, and said water, in said liquid mixture; a fluid flow path configured to convey the liquid mixture in a downstream direction from an acid catalyst stream in a hydrocarbon conversion process to the instrument; a separator configured to remove hydrocarbon present in a gas or liquid phase distinct from that of the liquid mixture; wherein said instrument, said other instrument, and said temperature detector, comprise a multi-channel spectrometer, having at least three channels.

2. The apparatus of claim 1, comprising a filter module communicably coupled to said processor, said filter configured to mathematically filter said temperature compensated concentration.

3. The apparatus of claim 1, wherein the at least three channels are configured for generating information corresponding to three mutually distinct parameters of the liquid mixture.

4. The apparatus of claim 3, wherein the temperature of the liquid mixture is determined inferentially.

5. The apparatus of claim 1, wherein the separator is disposed at or upstream of at least one of said instruments within said fluid flow path.

6. The apparatus of claim 5, wherein the gas/liquid separator is disposed upstream of both of said instrument and said other instrument within said fluid flow path.

7. The apparatus of claim 5, configured to generate said temperature compensated concentration while the liquid mixture flows continuously through the fluid flow path.

8. The apparatus of claim 1, wherein the fluid flow path comprises parallel legs and the continuously flowing liquid mixture alternates between said legs.

9. The apparatus of claim 1, wherein said model comprises a model data set of expected outputs from the first and second instruments when measuring liquid samples having a plurality of known concentrations of acid, acid-soluble-oil (ASO), and water.

10. The apparatus of claim 1, wherein the acid in said acid catalyst is hydrofluoric acid (HF) acid.

11. The apparatus of claim 1, wherein the acid in said acid catalyst is sulfuric acid (SA).

12. A method for on-line concentration determination of at least one component in an acid catalyst for hydrocarbon conversion containing unknown concentrations of an acid, an acid-soluble-oil (ASO), and water, said method comprising: (a) supplying the acid catalyst to an instrument configured to have responsivities to concentrations of one of the acid, ASO, and water, substantially independent of the concentrations of the others of the acid catalyst, ASO, and water; (b) supplying the acid catalyst to a temperature detector; (c) measuring a property of the acid catalyst using the instrument; (d) generating temperature data for the acid catalyst using the temperature detector; (e) capturing, with a processor, data generated by the instrument and the temperature detector; (f) determining, with the processor, using the data in combination with a model of responsivities to various concentrations of the acid, ASO, and water at various temperatures, a temperature compensated concentration of at least one of said acid, said ASO, and said water, in said acid catalyst; (g) using a separator configured to remove phase separated hydrocarbons present in the acid catalyst to separate the hydrocarbon present in a gas or liquid phase distinct from the acid catalyst prior to effecting said measuring (c), wherein said separating is effected while conveying the acid catalyst substantially continuously in a downstream direction; and (h) using an instrument, an other instrument, and a temperature detector, in the form of a multi-channel spectrometer, having at least three channels.

13. The method of claim 12, comprising filtering, with a filter module communicably coupled to the processor, the temperature compensated concentration.

14. The method of claim 12, wherein said supplying (a) further comprises supplying the acid catalyst to the other instrument configured to have mutually distinct responsivities to concentrations of the acid, ASO, and water relative to said instrument; wherein said measuring (c) comprises using the other instrument; said capturing (e) comprises capturing data from said other instrument; and said determining (f) comprises using the data generated by the other instrument.

15. The method of claim 14, further comprising using a model that includes a model data set of expected outputs from the instrument and the other instrument when the instruments are used to measure liquid samples having a plurality of known concentrations of acid catalyst, acid-soluble-oil (ASO), and water.

16. The method of claim 12, further comprising using a multi-channel spectrometer in which the at least three channels are configured for generating information corresponding to three mutually distinct parameters of the liquid mixture.

17. The method of claim 16, further comprising inferentially determining the temperature of the liquid mixture.

18. The method of claim 12, wherein said separating is effected using an alternating stop flow via parallel flow paths.

19. The method of claim 12, further comprising obtaining an acid catalyst sample from an acid catalyst stream in a hydrocarbon conversion process.

20. The method of claim 12, using an acid catalyst comprising hydrofluoric acid (HF) acid.

21. The method of claim 12, using an acid catalyst comprising sulfuric acid (SA).

* * * * *